United States Patent
Shimohata

(10) Patent No.: US 10,924,640 B2
(45) Date of Patent: Feb. 16, 2021

(54) IMAGE PICKUP MODULE AND ENDOSCOPE INCLUDING IMAGE PICKUP MODULE IN WHICH BONDING JUNCTION BETWEEN IMAGE PICKUP PORTION AND SIGNAL CABLE IS RESIN-SEALED BY CURABLE RESIN

(71) Applicant: OLYMPUS CORPORATION, Tokyo (JP)

(72) Inventor: Takahiro Shimohata, Shiojiri (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 16/661,315

(22) Filed: Oct. 23, 2019

(65) Prior Publication Data

US 2020/0059576 A1 Feb. 20, 2020

Related U.S. Application Data

(63) Continuation of application No. PCT/JP2017/016150, filed on Apr. 24, 2017.

(51) Int. Cl.
*H04N 5/225* (2006.01)

(52) U.S. Cl.
CPC ... *H04N 5/2251* (2013.01); *H04N 2005/2255* (2013.01)

(58) Field of Classification Search
CPC .. A61B 1/00064; A61B 1/0011; A61B 1/0676
See application file for complete search history.

(56) References Cited

U.S. PATENT DOCUMENTS

| 2018/0041666 A1* | 2/2018 | Nakayama | ........... H05K 3/4092 |
| 2019/0069767 A1* | 3/2019 | Mikami | ................. A61B 1/005 |

FOREIGN PATENT DOCUMENTS

| JP | 05-154099 A | 6/1993 |
| JP | 2002-204775 A | 7/2002 |
| JP | 2015-066297 A | 4/2015 |
| JP | 2015-107218 A | 6/2015 |
| JP | 6041285 B1 | 12/2016 |

OTHER PUBLICATIONS

International Search Report dated Jun. 20, 2017 received in PCT/JP2017/016150.

* cited by examiner

*Primary Examiner* — Jayanti K Patel
*Assistant Examiner* — Christopher Kingsbury Glover
(74) *Attorney, Agent, or Firm* — Scully, Scott, Murphy & Presser, P.C.

(57) ABSTRACT

An endoscope includes an image pickup apparatus disposed in a rigid distal end portion. The image pickup apparatus is provided with: an image pickup sensor with an external electrode being disposed on a rear face; a signal cable, a distal end portion of which is bonded to the external electrode of the imager; and resin sealing a bonding junction between the external electrode and the distal end portion, where the resin is accommodated in a space formed when the rear face is projected in a direction of an optical axis of the imager. A rear end position of the resin is defined by a resin stopping portion of the signal cable.

15 Claims, 5 Drawing Sheets

1

IMAGE PICKUP MODULE AND ENDOSCOPE INCLUDING IMAGE PICKUP MODULE IN WHICH BONDING JUNCTION BETWEEN IMAGE PICKUP PORTION AND SIGNAL CABLE IS RESIN-SEALED BY CURABLE RESIN

CROSS REFERENCE TO RELATED APPLICATION

This application is a continuation application of PCT/JP2017/016150 filed on Apr. 24, 2017, the entire contents of which are incorporated herein by this reference.

BACKGROUND OF THE INVENTION

1. Field of the Invention

The present invention relates to an endoscope with an image pickup apparatus in which a bonding junction between an imager and a signal cable is resin-sealed, the image pickup apparatus being disposed in an insertion portion; the image pickup apparatus in which the bonding junction between the imager and the signal cable is resin-sealed; and a method for manufacturing the endoscope with the image pickup apparatus in which the bonding junction between the imager and the signal cable is resin-sealed, the image pickup apparatus being disposed in the insertion portion.

2. Description of the Related Art

For the purpose of reducing invasiveness, it is important to shorten and miniaturize a rigid distal end portion of an endoscope, and development of a short and small image pickup apparatus has been made.

Japanese Patent Application Laid-Open Publication No. 2015-66297 discloses an endoscope with an image pickup apparatus disposed in an insertion portion. The image pickup apparatus and a signal cable are connected via a wiring board. A bonding junction between the signal cable and the wiring board is sealed with adhesive resin.

SUMMARY OF THE INVENTION

In an endoscope of an embodiment of the present invention, an image pickup signal outputted by an imager of an image pickup apparatus disposed in a rigid distal end portion is transmitted by at least one signal cable. The image pickup apparatus is provided with: the imager having a light receiving face and a rear face on an opposite side of the light receiving face, with an external electrode being disposed on the rear face; the signal cable, a distal end portion of which is bonded to the external electrode of the imager or a bonding electrode of another member electrically connected to the external electrode; and resin sealing a bonding junction between the external electrode or the bonding electrode and the distal end portion and being accommodated in a space formed when the rear face is supposed to be extended in a direction of an optical axis of the imager; wherein a rear end position of the resin is defined by a ring-shaped groove of the signal cable.

An image pickup apparatus of the embodiment is provided with: the imager having a light receiving face and a rear face on an opposite side of the light receiving face, with an external electrode being disposed on the rear face; at least one signal cable, a distal end portion of which is bonded to the external electrode of the imager or a bonding electrode of another member electrically connected to the external electrode; resin sealing a bonding junction between the external electrode or the bonding electrode and the distal end portion and being accommodated in a space formed when the rear face is supposed to be extended in a direction of an optical axis of the imager; wherein a rear end position of the resin is defined by a ring-shaped groove of the signal cable.

An endoscope manufacturing method of the embodiment is a method for manufacturing an endoscope transmitting an image pickup signal outputted by an imager of an image pickup apparatus disposed in a rigid distal end portion by at least one signal cable, the method including: a distal end portion of the signal cable being bonded to an external electrode of the imager having a light receiving face and a rear face on an opposite side of the light receiving face, the external electrode being disposed on the rear face, or a bonding electrode of another member electrically connected to the external electrode; uncured liquid resin being disposed, the resin sealing a bonding junction between the external electrode or the bonding electrode and the distal end portion and being accommodated in a space formed when the rear face is supposed to be extended in a direction of an optical axis of the imager; the resin being curing-treated; a ring-shaped groove being formed on the signal cable before the resin is disposed; and a rear end position of the liquid resin being defined by the ring-shaped groove when the liquid resin is disposed.

DETAILED DESCRIPTION OF THE PREFERRED EMBODIMENTS

First Embodiment

Figure 1:
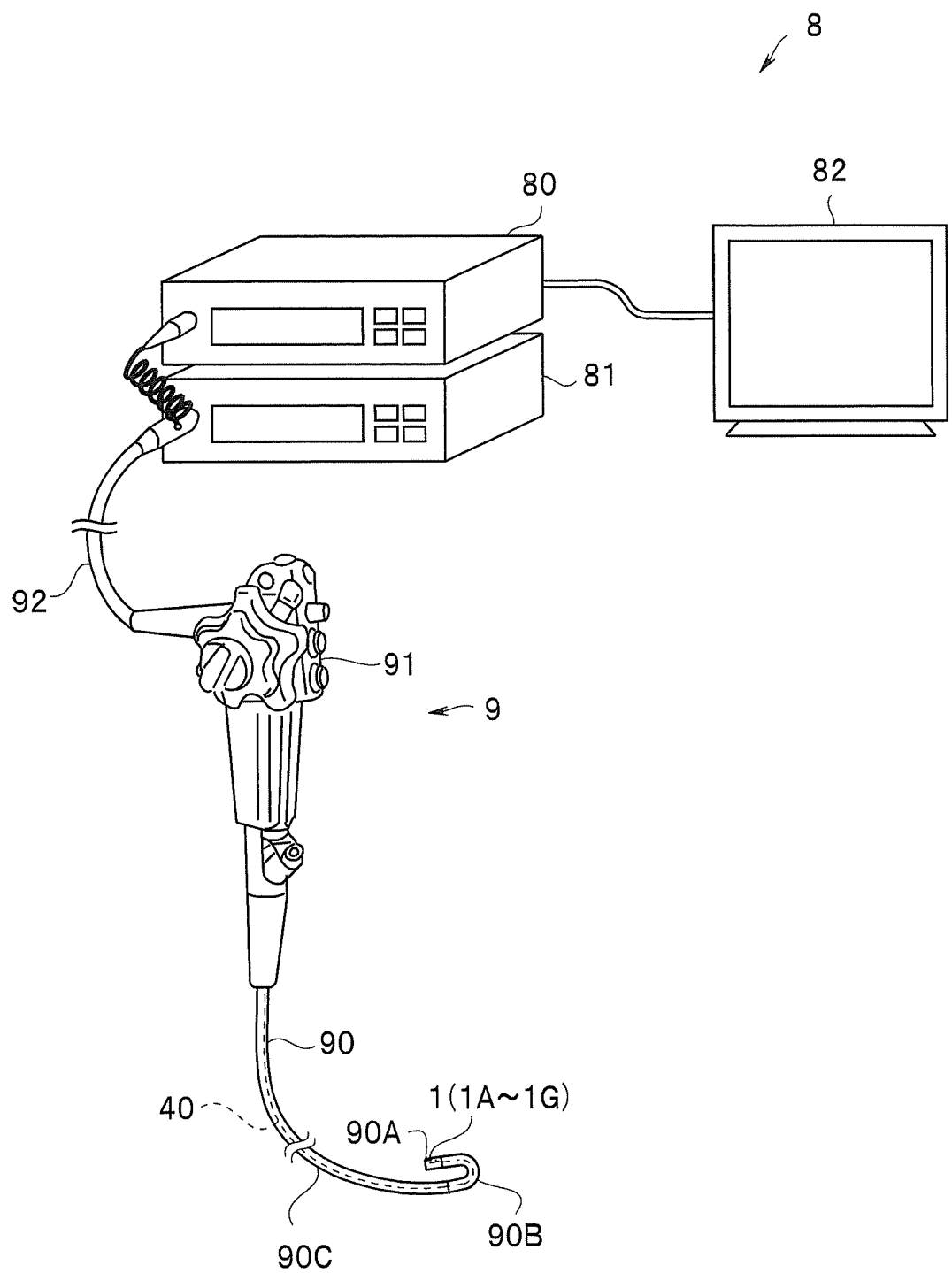
FIG. 1 is a perspective view of an endoscope system that includes an endoscope of a first embodiment.

As shown in FIG. 1, an endoscope system 8 that includes an endoscope 9 of the present embodiment is provided with the endoscope 9, a processor 80, a light source apparatus 81 and a monitor 82. The endoscope 9 has an insertion portion 90, an operation portion 91 and a universal cord 92. The insertion portion 90 of the endoscope 9 is inserted into a subject's body cavity to photograph the subject's in-vivo image and output an image signal.

The insertion portion 90 is configured with a rigid distal end portion 90A on which an image pickup module 1, which is an image pickup apparatus, is disposed, a freely bendable bending portion 90B connectedly provided on a proximal end side of the rigid distal end portion 90A, and a flexible portion 90C connectedly provided on a proximal end side of the bending portion 90B. The bending portion 90B bends by operating the operation portion 91. Note that the endoscope 9 may be a rigid endoscope.

On a proximal end side of the insertion portion 90 of the endoscope 9, the operation portion 91 provided with various kinds of buttons for operating the endoscope 9 is disposed.

The light source apparatus 81 has, for example, a white LED. Illumination light emitted by the light source apparatus 81 is guided to the rigid distal end portion 90A via the universal cord 92 and a light guide (not shown) inserted in the insertion portion 90 to illuminate an object.

The endoscope 9 has the insertion portion 90, the operation portion 91 and the universal cord 92; and an image pickup signal outputted by the image pickup module 1 disposed in the rigid distal end portion 90A of the insertion portion 90 is transmitted through a signal cable 40 inserted in the insertion portion 90. Since the image pickup module 1 is ultraminiature, the rigid distal end portion 90A of the insertion portion 90 in the endoscope 9 has a small diameter and is minimally invasive.

Furthermore, as described later, since the image pickup module 1 is small-sized and is easy to manufacture, the endoscope 9 is easy to manufacture.

Second Embodiment

Figure 2:
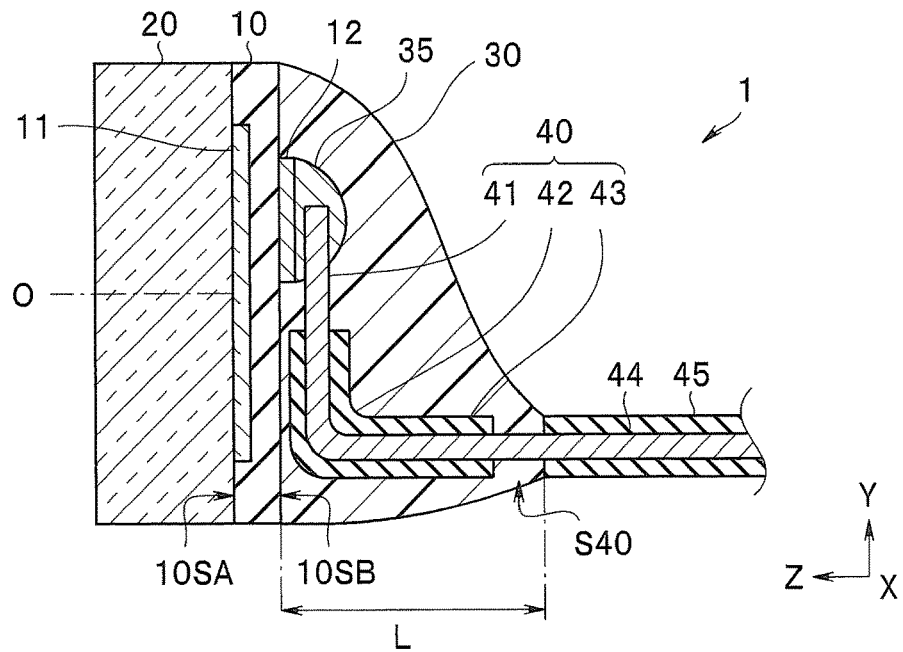
FIG. 2 is a cross-sectional view of an image pickup module of a second embodiment.
Figure 3:
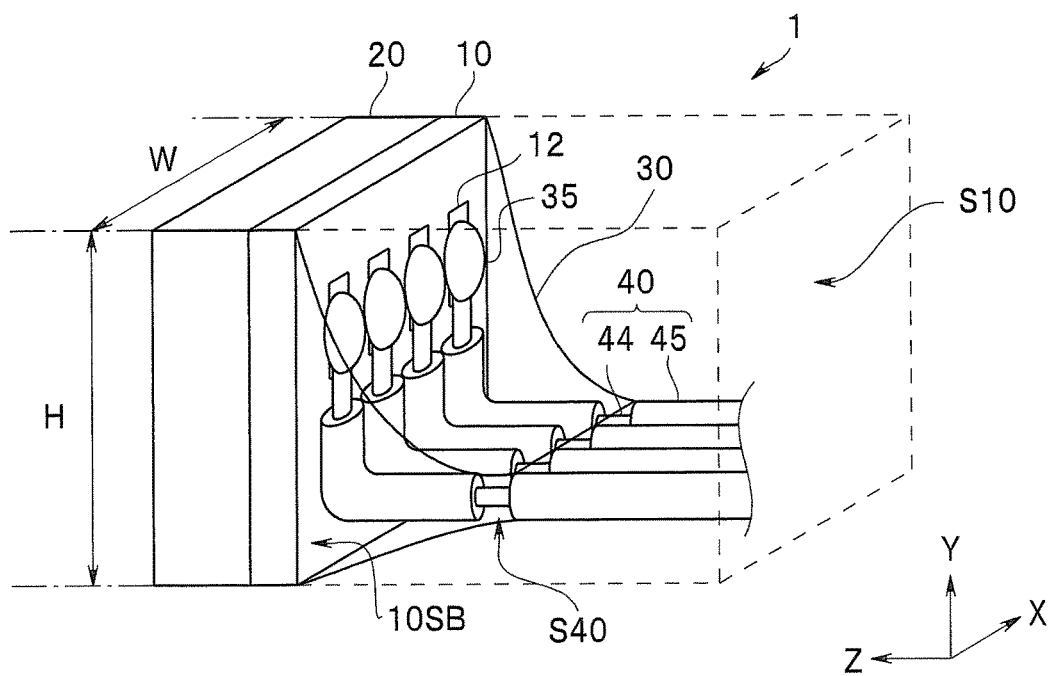
FIG. 3 is a perspective view of the image pickup module of the second embodiment.

As shown in FIGS. 2 and 3, the image pickup module 1 of the present embodiment is provided with an image pickup device 10, which is an imager, cover glass 20, resin 30 and the signal cable 40.

Note that, in the description below, drawings based on each embodiment are schematic. A relationship between a thickness and a width of each portion, a thickness ratio among respective portions and the like are different from actual ones. Among the mutual drawings, portions that are different in a mutual dimensional relationship and ratio may be included. A part of components may not be shown, and reference numerals may not be given to the components.

The image pickup device 10 has a light receiving face 10SA having a light receiving portion 11, and a rear face 10SB on an opposite side of the light receiving face 10SA. The light receiving portion 11 is connected to a plurality of external electrodes 12 disposed on the rear face 10SB, for example, via through wiring (not shown).

The cover glass 20 is made to adhere to the light receiving face 10SA of the image pickup device 10 via an adhesive layer (not shown). Note that the cover glass 20 is not a required component of the image pickup module 1.

The signal cable 40 includes a distal end portion 41, a bending portion 42, an extended portion 43 extended rearward from the bending portion 42. The signal cable 40 is a single wire or a simple wire that is configured with a core wire 44 and an outer cover 45 covering the core wire 44. The signal cable 40 may be a shielded cable having a shielded wire.

On the distal end portion 41 of the signal cable 40, the outer cover 45 is stripped, and the core wire 44 is exposed. The distal end portion 41 is bonded with the external electrodes 12, for example, with solder 35. In order to guarantee strength of a bonding junction, the distal end portion 41 is arranged in parallel to the rear face 10SB of the image pickup device 10. Since the bending portion 42 is bent almost at right angles, the extended portion 43 is extended rearward.

Note that, by bonding a cable end face of the signal cable 40 to the external electrodes 12, the signal cable 40 is arranged vertical to the rear face 10SB of the image pickup device 10, and the extended portion 43 may be extended rearward as it is, without the bending portion 42 being provided.

The resin 30 is sealing resin sealing a bonding junction between the distal end portion 41 of the signal cable 40 and the external electrodes 12 and covering the bending portion 42 and a part of the extended portion 43 of the signal cable 40.

The resin 30 is accommodated inside a space S10 formed when the rear face 10SB of the image pickup device 10, which is an image pickup portion, is supposed to be extended in an optical axis direction. In other words, an outer diameter (XY dimensions) of the image pickup module 1 does not become large with the resin 30. Note that the resin 30 may be transparent or light-shielding.

In the image pickup module 1, the extended portion 43 extended rearward from the bending portion 42 of the signal cable 40 is provided with a resin stopping portion S40 which is a ring-shaped groove. The resin stopping portion S40 is an area where the outer cover 45 is stripped, and the core wire 44 is exposed.

A rear end position of the resin 30 is defined by the resin stopping portion S40 of the extended portion 43. Therefore, a rigid length L along which the rigid resin 30 is disposed is short, and the image pickup module 1 is short and small.

In other words, the resin 30 is curable resin and disposed on the rear face 10SB in an uncured liquid state. Though the liquid resin 30 spreads rearward of the extended portion 43 of the signal cable 40, the resin 30 does not spread rearward of the resin stopping portion S40 due to interfacial tension. The liquid resin 30 becomes a rigid solid by UV curing treatment or thermosetting treatment.

As the resin 30, various kinds of curable resins such as epoxy resin and silicone resin can be used if the resins are fluid liquid when they are in an uncured state.

Note that, for example, when an outer diameter of the signal cable 40 and a thickness of the outer cover 45 are 98 μm and 25 μm, respectively, a depth of the groove of the resin stopping portion S40 is 25 μm. A width of the groove is preferably between 50 μm and 300 μm, including 50 μm and 300 μm. If the width is within the above range, it is possible to prevent resin in a liquid state from spreading, and it is possible to realize shortening and miniaturization.

Formation of the groove, that is, stripping of the outer cover 45 can be easily performed, for example, by laser radiation processing. The formation of the groove may be performed before or after bonding the signal cable 40 to the image pickup device 10.

In a method for manufacturing an endoscope transmitting an image pickup signal outputted by an imager of an image pickup apparatus disposed in a rigid distal end portion by at least one signal cable, a distal end portion of the signal cable is bonded to an external electrode of the imager having a light receiving face and a rear face on an opposite side of the light receiving face, the external electrode being disposed on the rear face, or a bonding electrode of another member electrically connected to the external electrode; uncured liquid resin is disposed, the resin sealing a bonding junction between the external electrode or the bonding electrode and the distal end portion and being accommodated in a space formed when the rear face is supposed to be extended in a direction of an optical axis of the imager; the resin is curing-treated; a ring-shaped groove is formed on the signal cable before the resin is disposed; and a rear end position of the liquid resin is defined by the ring-shaped groove when the liquid resin is disposed.

Modifications of Second Embodiment

Since image pickup modules 1A to 1E of modifications of the second embodiment are similar to the image pickup module 1 and have the same effects, the same reference numerals are given to components having the same functions, and description of the components will be omitted.

Modification 1 of Second Embodiment

Figure 4:
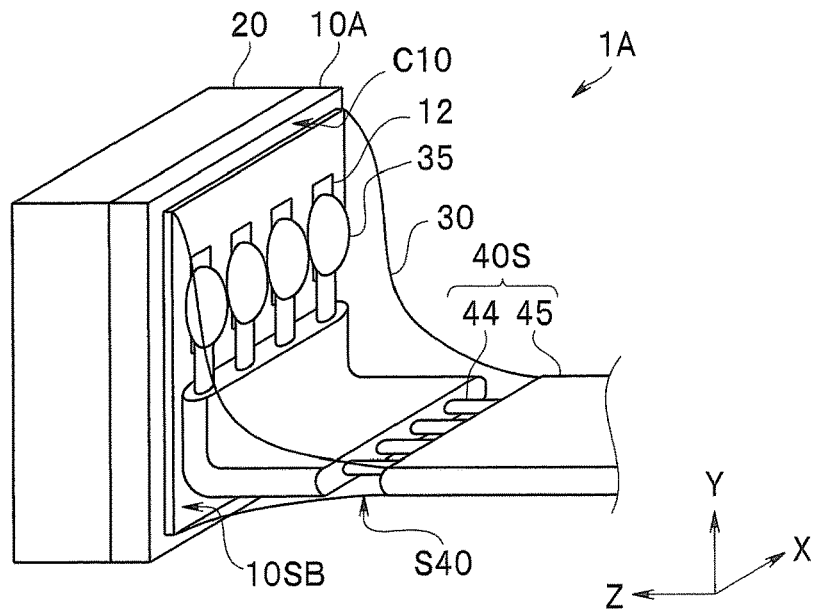
FIG. 4 is a perspective view of an image pickup module of a modification 1 of the second embodiment.

As shown in FIG. 4, the image pickup module 1A of the present modification has a flat cable 40S that includes a plurality of core wires 44. The resin stopping portion S40 is an area where the outer cover 45 of the flat cable 40S is stripped, and the plurality of core wires 44 are exposed. The plurality of external electrodes 12 of the image pickup device 10 are arranged so that positions of the external electrodes 12 correspond to positions of the plurality of core wires 44.

Therefore, in the image pickup module 1A, it is easy to bond the core wires 44 to the external electrodes 12.

The rear face 10SB of an image pickup device 10A has a notch C10 on a circumferential portion. Therefore, the resin 30 in a liquid state is certainly prevented from spreading to side faces due to surface tension. The notch C10 can be easily formed by a step cut method in which, when cutting and dividing an image pickup wafer including a plurality of image pickup devices, two kinds of dicing blades with different widths are used.

Modification 2 of Second Embodiment

Figure 5:
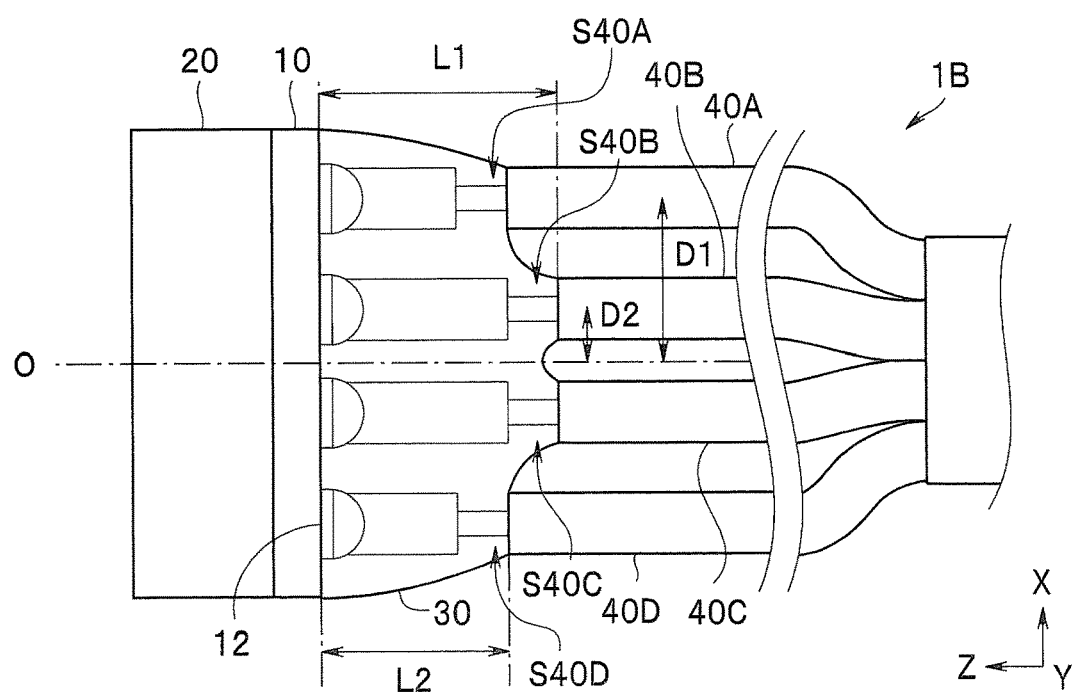
FIG. 5 is a top view of an image pickup module of a modification 2 of the second embodiment.

As shown in FIG. 5, in the image pickup module 1B of the present modification, lengths L1 and L2 from bonding junctions between a plurality of signal cables 40A to 40D and the image pickup device 10 to resin stopping portions S40A to S40D are different from each other. In other words, the length L1 for the signal cables 40B and 40C is longer than the length L2 for the signal cables 40A and 40D.

The signal cables 40B and 40C are arranged on an inner side of the signal cables 40A and 40D. In other words, a distance D2 between each of the extended portions of the signal cables 40B and 40C and an extension line of an optical axis O is shorter than a distance D1 between each of the extended portions of the signal cables 40A and 40D and the extension line of the optical axis O. In other words, the signal cables 40B and 40C are closer to the extension line of the optical axis O of the image pickup device 10 than the signal cables 40A and 40D.

In other words, a length from the bonding junction to the ring-shaped groove for each of the plurality of signal cables differs according to the distance between the signal cable and the extension line of the optical axis O, and the length is longer for a signal cable closer to the extension line.

The resin 30 in a liquid state easily spreads to an inner side due to surface tension when the resin 30 is disposed. As for the image pickup module 1B, since positions of the resin stopping portions S40A to S40D are set according to a spread state of the resin 30, it is possible to certainly prevent spread of the resin 30 at the resin stopping portions S40A to S40D.

Modification 3 of Second Embodiment

Figure 6:
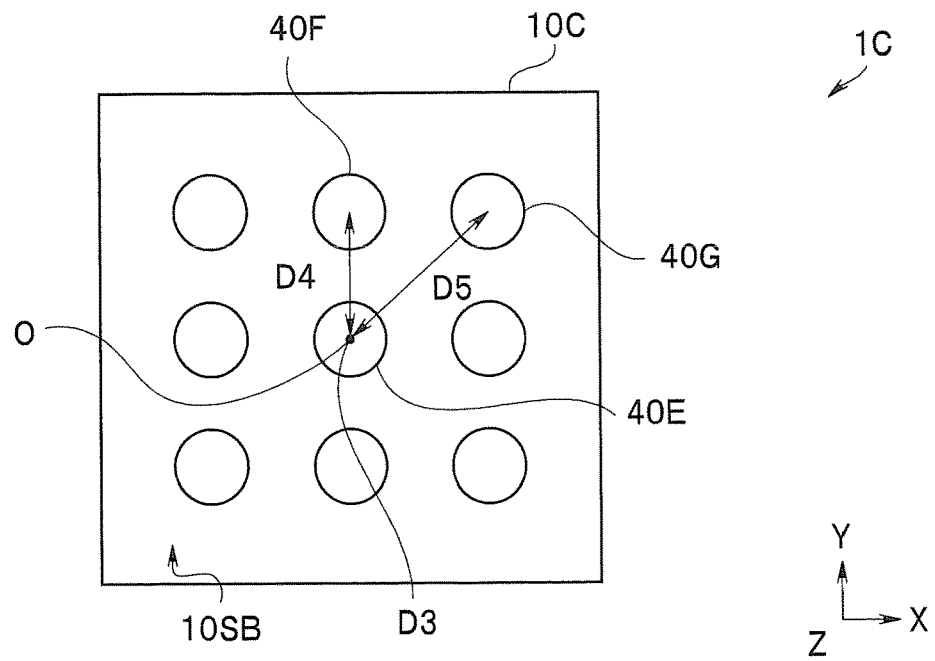
FIG. 6 is a schematic rear view of an image pickup module of a modification 3 of the second embodiment.

FIG. 6 is a schematic rear view when the image pickup module 1C of the present modification is seen from a rear face side.

In the image pickup module 1B and the like, the plurality of external electrodes 12 on the rear face 10SB of the image pickup device 10 are one-dimensionally arranged being lined up on a straight line. In comparison, in the image pickup module 1C, a plurality of external electrodes (not shown) are two-dimensionally arranged on the rear face 10SB of the image pickup device 10C in a matrix. A plurality of signal cables 40E to 40G are also two-dimensionally arranged.

For example, the signal cable 40E is arranged on the extension line of the optical axis O, and a distance D3 to the extension line is zero. A distance between the signal cable 40F and the extension line is D4, and a distance between the signal cable 40G and the extension line is D5.

As for the length L of each of the signal cables 40E to 40G to the resin stopping portions, since the condition: distance D3<distance D4<distance D5 is satisfied, the length L is set the longest for the signal cable 40E and set the shortest for the signal cable 40G.

In other words, the plurality of external electrodes 12 are two-dimensionally arranged on the rear face 10SB; the length from the bonding junction to the ring-shaped groove for each of the plurality of signal cables differs according to the distance between the signal cable and the extension line of the optical axis O; and the length is longer for a signal cable closer to the extension line.

The image pickup module 1C has the same effects as the image pickup module 1B.

Modifications 4 and 5 of Second Embodiment

Figure 7:
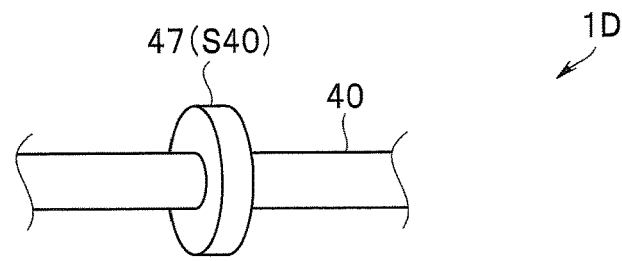
FIG. 7 is a perspective view of a signal cable of an image pickup module of a modification 4 of the second embodiment.

As shown in FIG. 7, in the image pickup module 1D of a modification 4, the resin stopping portion S40 of the signal cable 40 is a ring-shaped projecting portion 47. The projecting portion 47 may be a different member different from the signal cable 40, for example, an O-shaped ring or wound film. The projecting portion 47 may be a part of the signal cable 40, for example, an area where the outer cover is stripped around the resin stopping portion S40.

In an endoscope having the image pickup module 1D and a method for manufacturing the image pickup module 1D, the ring-shaped projecting portion 47 is disposed on the signal cable 40 before the uncured liquid resin 30 is disposed, and the rear end position of the resin 30 is defined by the ring-shaped projecting portion 47 when the resin 30 is disposed.

Figure 8:
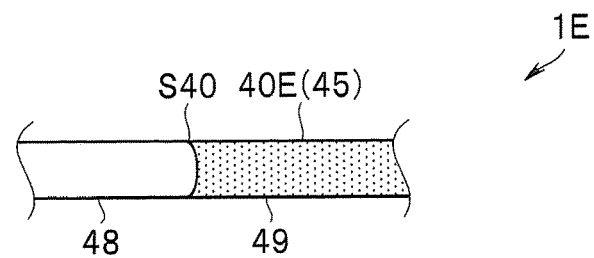
FIG. 8 is a perspective view of a signal cable of an image pickup module of a modification 5 of the second embodiment.

As shown in FIG. 8, in the image pickup module 1E of a modification 5, surface tension of the outer cover 45 of the signal cable 40E changes due to surface treatment at the resin stopping portion S40.

When resin in a liquid state is hydrophilic, a front area 48 and a rear area 49 of the signal cable 40E are hydrophilic and hydrophobic, respectively. For example, when the outer cover 45 is hydrophobic fluororesin, the front area 48 may be plasma hydrophilic-treated or surface roughening treated.

In an endoscope having the image pickup module 1E and a method for manufacturing the image pickup module 1E, an area where surface tension changes is formed on the outer cover 45 of the signal cable 40E that includes the core wire 44 and the outer cover 45, before the uncured liquid resin 30 is disposed, and the rear end position of the resin 30 is defined by the area where the surface tension changes when the resin 30 is disposed.

Third and Fourth Embodiments

Since an image pickup module 1F of a third embodiment and an image pickup module 1G of a fourth embodiment are similar to the image pickup module 1 and have the same effects, the same reference numerals are given to components having the same functions, and description of the components will be omitted.

Third Embodiment

Figure 9:
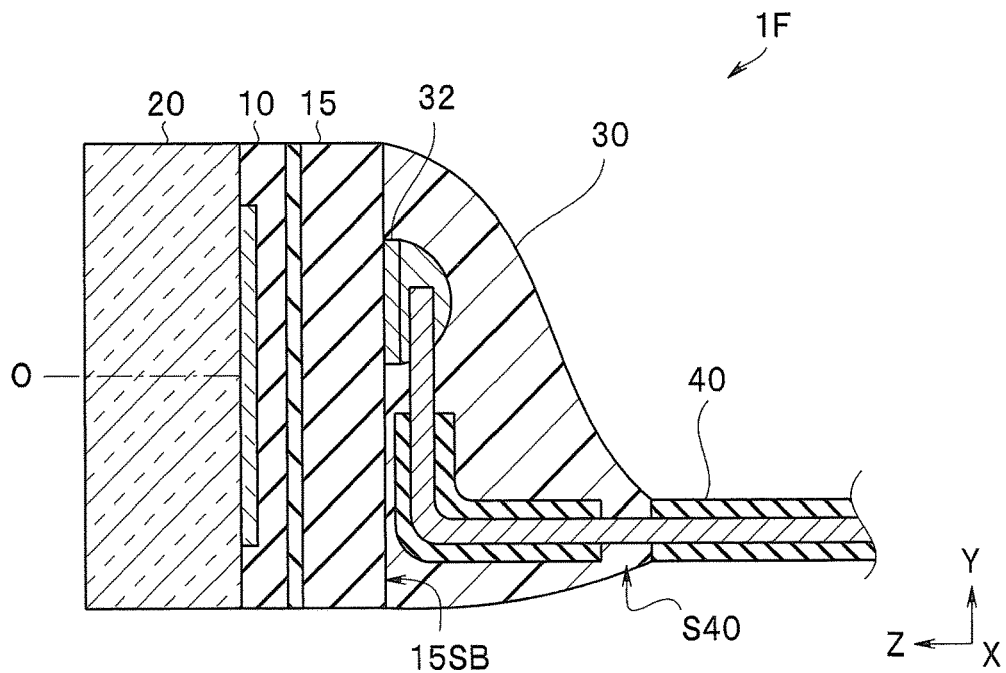
FIG. 9 is a cross-sectional view of an image pickup module of a third embodiment.

As shown in FIG. 9, in the image pickup module 1F, an interposer 15, which is another member, is disposed on the rear face 10SB of the image pickup device 10.

Bonding electrodes 32 on a rear face 15SB of the interposer 15 are electrically connected to external electrodes (not shown) of the image pickup device 10. The signal cable 40 is bonded to the bonding electrodes 32.

Figure 10:
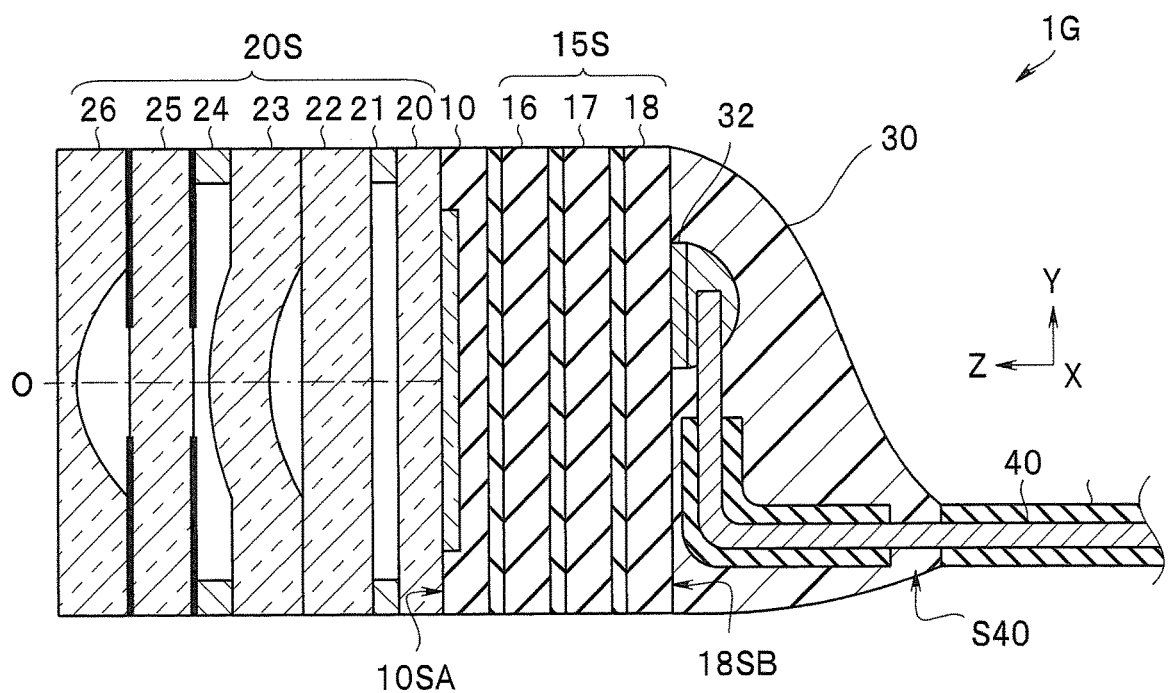
FIG. 10 is a cross-sectional view of an image pickup module of a fourth embodiment.

Note that the other member disposed on the rear face 10SB of the image pickup device 10 may be at least are of a wiring board, a semiconductor device and a semiconductor device stack 15S (see FIG. 10).

Fourth Embodiment

As shown in FIG. 10, in the image pickup module 1G, the semiconductor device stack 15S that is configured with a plurality of laminated semiconductor devices 16, 17 and 18 and that is the other member is disposed on the rear face 10SB of the image pickup device 10. On the light receiving face 10SA, an optical device stack 20S configured with a plurality of laminated optical devices 20 to 26 is disposed.

For example, each of the semiconductor devices 16, 17 and 18 of the semiconductor device stack 15S may be a device on which a thin-film capacitor or a thin-film inductor is formed, or a device on which semiconductor circuits such as an AD conversion circuit and a signal processing circuit are formed.

The optical device stack 20S is configured with the cover glass 20, a spacer 21, a filter 22, a lens 23, a spacer 24, aperture glass 25 and a lens 26.

The semiconductor device stack 15S is fabricated by cutting a bonded semiconductor wafer configured with a plurality of laminated and bonded semiconductor wafers each of which includes semiconductor devices 16 to 18. Similarly, the optical device stack 20S is fabricated by cutting a bonded optical device wafer configured with a plurality of laminated and bonded optical device wafers each of which includes optical devices 20 to 24.

The bonding electrodes 32 on a rearmost face 18SB of the semiconductor device stack 15S are electrically connected to external electrodes (not shown) of the image pickup device 10. The signal cable 40 is bonded to the bonding electrodes 32.

It goes without saying that the endoscope 9 having any of the image pickup modules 1A to 1G has the effects of the endoscope 9 having the image pickup module 1 and the effects of the image pickup modules 1A to 1G.

The present invention is not limited to the embodiments and the like stated above, but various kinds of changes, alterations and the like can be made within a range not changing the spirit of the present invention.

What is claimed is:

1. An endoscope comprising:
   an insertion section having a rigid distal end portion;
   an image pickup apparatus disposed in the rigid distal end portion, wherein the image pickup apparatus comprises an image pickup sensor configured to output an image pickup signal, the image pickup sensor having a light receiving face and a rear face on an opposite side of the light receiving face, with an external electrode being disposed on the rear face;
   a signal cable, a distal end portion of which is one of directly bonded to the external electrode of the image pickup sensor or indirectly bonded to the external electrode of the image pickup sensor through a bonding electrode of another member electrically connected to the external electrode; and
   resin configured to seal a bonding junction between the external electrode or the bonding electrode and the distal end portion of the signal cable, the resin being entirely accommodated in a space formed by projecting the rear face of the image pickup sensor in a direction of an optical axis of the image pickup sensor;
   wherein a rear end position of the resin in the optical axis direction is defined by a ring-shaped groove formed in the signal cable; and
   the resin is a curable resin and is disposed in the space in a liquid state, the ring-shaped groove being configured such that the resin does not spread rearward, in the optical axis direction, of the ring-shaped groove due to interfacial tension with the ring-shaped groove, and the resin becomes a rigid solid by a curing treatment.

2. The endoscope according to claim 1, wherein the signal cable includes a core wire and an outer cover, wherein the ring-shaped groove comprises a portion of the signal cable where the outer cover is removed.

3. The endoscope according to claim 1, wherein the signal cable includes the distal end portion, a bending portion and an extended portion extended rearward from the bending portion, and the ring-shaped groove being provided in the extended portion.

4. The endoscope according to claim 1, wherein:
   the signal cable comprises a plurality of signal cables, each having a ring-shaped groove, and
   a length from the bonding junction of each of the plurality of signal cables to each ring-shaped groove differs according to a distance between the signal cable and a center line of the plurality of cables in a direction orthogonal to the optical axis, and
   the length is longer for the signal cable of the plurality of signal cables which is closer to the center line.

5. The endoscope according to claim 1, wherein the other member is one or more of a wiring board, an interposer, a semiconductor device, or a semiconductor device stack.

6. An image pickup apparatus comprising:
   an image pickup module having an image pickup sensor configured to output an image pickup signal, the image pickup sensor having a light receiving face and a rear face on an opposite side of the light receiving face, with an external electrode being disposed on the rear face;
   at least one signal cable, a distal end portion of which is one of directly bonded to the external electrode of the image pickup sensor or indirectly bonded to the external electrode of the image pickup sensor through a bonding electrode of another member electrically connected to the external electrode; and
   resin configured to seal a bonding junction between the external electrode or the bonding electrode and the distal end portion of the signal cable, the resin being entirely accommodated in a space formed by projecting the rear face in a direction of an optical axis of the image pickup sensor;

wherein a rear end position of the resin in the optical axis direction is defined by a ring-shaped groove formed in the signal cable; and the resin is a curable resin and is disposed in the space in a liquid state, the ring-shaped groove being configured such that the resin does not spread rearward, in the optical axis direction, of the ring-shaped groove due to interfacial tension with the ring-shaped groove, and the resin becomes a rigid solid by a curing treatment.

7. The image pickup apparatus according to claim 6, wherein the signal cable includes a core wire and an outer cover, the ring-shaped groove comprises a portion of the signal cable where the outer cover is removed.

8. The image pickup apparatus according to claim 6, wherein the signal cable includes the distal end portion, a bending portion and an extended portion extended rearward from the bending portion, and the ring-shaped groove being provided in the extended portion.

9. The image pickup apparatus according to claim 6, wherein:
the signal cable comprises a plurality of signal cables, each having a ring-shaped groove, and
a length from the bonding junction of each of the plurality of signal cables to each ring-shaped groove differs according to a distance between the signal cable and a center line of the plurality of cables in a direction orthogonal to the optical axis, and
the length is longer for the signal cable of the plurality of signal cables which is closer to the center line.

10. The image pickup apparatus according to claim 6, wherein the other member is one or more of a wiring board, an interposer, a semiconductor device, or a semiconductor device stack.

11. A method for manufacturing an endoscope transmitting an image pickup signal outputted by an image pickup sensor of an image pickup apparatus disposed in a rigid distal end portion by at least one signal cable, the image pickup sensor having a light receiving face and a rear face on an opposite side of the light receiving face, an external electrode being disposed on the rear face, the method comprising:

one of bonding a distal end portion of the at least one signal cable directly to an external electrode of the image pickup sensor or indirectly to the external electrode of the image pickup sensor through a bonding electrode of another member electrically connected to the external electrode;

forming a ring-shaped groove on the at least one signal cable;

subsequent to the forming, disposing an uncured liquid resin to seal a bonding junction between the external electrode or the bonding electrode and the distal end portion, the resin being entirely accommodated in a space formed by projecting the rear face in a direction of an optical axis of the image pickup sensor, wherein a rear end position of the liquid resin in the optical axis direction being defined by the ring-shaped groove due to interfacial tension with the ring-shaped groove; and curing the resin in the space.

12. The endoscope manufacturing method according to claim 11, wherein the signal cable includes a core wire and an outer cover, and the forming comprises removing a portion of the outer cover to form the ring-shaped groove.

13. The endoscope manufacturing method according to claim 11, wherein the signal cable includes the distal end portion, a bending portion and an extended portion extended rearward from the bending portion, and the ring-shaped groove being provided in the extended portion.

14. The endoscope manufacturing method according to claim 11, wherein
the signal cable comprises a plurality of signal cables, each having a ring-shaped groove; and
a length from the bonding junction of each of the plurality of signal cables to each ring-shaped groove differs according to a distance between the signal cable and a center line of the plurality of cables in a direction orthogonal to the optical axis, and
the length is longer for the signal cable of the plurality of signal cables which is closer to the center line.

15. The endoscope manufacturing method according to claim 11, wherein the other member is one or more of a wiring board, an interposer, a semiconductor device, or a semiconductor device stack.

* * * * *